(12) United States Patent
Mavliev

(10) Patent No.: US 10,241,024 B1
(45) Date of Patent: Mar. 26, 2019

(54) SYSTEM AND METHOD FOR CHARACTERIZATION OF INCLUSIONS IN LIQUID SAMPLES

(71) Applicant: Rashid Mavliev, Campbell, CA (US)

(72) Inventor: Rashid Mavliev, Campbell, CA (US)

( * ) Notice: Subject to any disclaimer, the term of this patent is extended or adjusted under 35 U.S.C. 154(b) by 0 days.

(21) Appl. No.: 15/585,022

(22) Filed: May 2, 2017

Related U.S. Application Data

(60) Provisional application No. 62/330,626, filed on May 2, 2016.

(51) Int. Cl.
  *G01N 21/05* (2006.01)
  *G01N 15/14* (2006.01)

(52) U.S. Cl.
  CPC ......... *G01N 15/1404* (2013.01); *G01N 21/05* (2013.01)

(58) Field of Classification Search
  CPC .............. G01N 30/02; G01N 15/1459; G01N 2015/0288; G01N 21/05; G01N 35/1097; G01N 15/1484; G01N 2015/1486; G01N 2021/0346; G01N 15/0205; G01N 15/1404; G01N 21/64; G01N 30/466; G01N 15/0255
  See application file for complete search history.

(56) References Cited

U.S. PATENT DOCUMENTS

| | | | |
|---|---|---|---|
| 5,110,208 A | 5/1992 | Sreepada et al. | |
| 7,738,101 B2 | 6/2010 | Mavliev | |
| 8,004,669 B1 * | 8/2011 | Kim | G01N 21/11 356/244 |
| 2004/0095574 A1 * | 5/2004 | Turner | G01N 15/1404 356/244 |
| 2006/0263829 A1 | 11/2006 | Evans et al. | |
| 2007/0229823 A1 | 10/2007 | Sung et al. | |
| 2009/0213382 A1 * | 8/2009 | Tracy | G01N 21/253 356/445 |
| 2012/0307244 A1 * | 12/2012 | Sharpe | G01N 15/1012 356/338 |
| 2013/0114068 A1 * | 5/2013 | Lim | G01N 21/07 356/39 |
| 2014/0152978 A1 | 6/2014 | Carr et al. | |

FOREIGN PATENT DOCUMENTS

CN  101529572 A  9/2009

* cited by examiner

*Primary Examiner* — Michael P Stafira
(74) *Attorney, Agent, or Firm* — Kwan & Olynick LLP

(57) ABSTRACT

Described are systems and methods for optical characterization of inclusions, such as solids and liquids, in liquid samples. An inclusion characterization system may include a radiation source, a radiation detector, a sample optical cell, and a sample delivery mechanism. The radiation detector may be configured to perform time resolved measurements. The sample may be delivered to the sample optical cell by the sample delivery mechanism at a flow rate set for preserving the sample integrity (i.e., the transport rate). The inclusion characterization in the sample may be performed at flow rates set for sample analysis (i.e., the analysis rate). The analysis rate may differ from the transport rate. The rate difference may be achieved by diverting only a portion of the overall sample into the sample optical cell. Also provided are examples of disengagement of sample transport and analysis flow rates.

20 Claims, 10 Drawing Sheets ered patent application 62/330,626, in its entirety.

SYSTEM AND METHOD FOR CHARACTERIZATION OF INCLUSIONS IN LIQUID SAMPLES

CROSS-REFERENCE TO RELATED APPLICATIONS

This application claims the benefit under 35 U.S.C. § 119(e) of U.S. Provisional Patent Application 62/330,626, entitled: "SYSTEM AND METHOD FOR CHARACTERIZATION OF INCLUSIONS IN LIQUID SAMPLES" filed on May 2, 2016, which is incorporated herein by reference in its entirety.

BACKGROUND

The subject matter presented herein relates generally to the field of detection and characterization of inclusions in liquid samples.

Liquid samples with high concentrations of inclusions (e.g., solid inclusions or liquid inclusions) are widely used in science and industry. Some examples of such samples include, but are not limited to, slurries used in chemical mechanical planarization (CMP) processes in the semiconductor industry and emulsions used in the pharmaceutical industry and other industries. Accurate characterization of such liquid samples, such as determining inclusion concentrations, may be important.

Yet, such characterization may be difficult. For example, variations in particle sizes may skew concentration measurements. Furthermore, sample flow rates may impact characterization accuracy. Therefore, a need exists for a system and a method for characterization of inclusions in liquid samples.

SUMMARY

Provided are a system and method of analyzing of inclusions in liquid samples, in particular liquid samples having concentrations of inclusions greater than $10^6$ particles per milliliter.

In some embodiments, a method of characterizing a liquid sample comprises delivering the sample to a sample optical cell and analyzing the sample using a detector. The detector may receive a signal from the sample, when, for example, the sample is exposed to the radiation source. For example, the sample may be exposed to a light source, and the light scattered from the sample may be analyzed to determine the concentration and size distribution of inclusions in the sample.

In some embodiments, the sample is delivered to the sample optical cell by a sample delivery mechanism at a flow rate selected for preserving the sample integrity, which may be referred to as a transport rate. The inclusion characterization of the sample is performed at a flow rate selected for the sample analysis, which may be referred to as an analysis rate. The two rates may differ from each other. The selection of each flow rate may be determined based on the sample or, more specifically, based on the characteristics of the sample.

In some embodiments, the analysis rate may also be a function of the analyzing parameters. For example, when single optical particle sizing (SPOS) is used for the sample analysis, the signal strength and measured number concentration strongly depend on the analysis flow rate. Bigger sample volume is surveyed per given observation time at higher flow rates, as a result more particles may be counted to improve the statistics at low concentration particles detection. The light scattered or obscured signal is lower at higher flow rates so the sensor operational range can be shifted toward larger inclusion sizes, such as 1 um and above, in some embodiments. Conversely, the operation at lower flow rates, such as 0.5-2 ml/min, enables measurements higher concentrations, such as $10^8$ particles per ml and above, and smaller inclusion sizes. The two analysis flow rates may differ significantly from each other thus increasing the dynamic range of measurable size and concentration of inclusions. The selection of each flow rate may be determined based on the sample or, more specifically, based on the characteristics of the sample.

In some embodiments, the analysis flow rate may be achieved by diverting only a portion of the liquid sample into the sample optical cell. This diverting operation may be also referred to as splitting of the incoming sample flow into two sub-flows, one of which is analyzed for inclusion characterization, such as concentration of inclusions, size of inclusions, and the like. For example, the sample can be delivered to the system at a flow rate of 30 ml/min, of which 3 ml/min may go to the measurement point of the sample optical cell and the remaining 27 ml/min of the sample may bypass the sample optical cell.

In some embodiments, the liquid sample is delivered at a first flow rate selected to keep the sample integrity. Once the sample is inside the particle monitoring system, the flow rate may be changed to a second flow rate selected for sample analysis. The second flow rate may be only kept for the duration necessary for the sample analysis but not sufficient to negatively impact the sample integrity. For example, the second flow rate may be less than the first flow rate. In some embodiments, the second flow rate may be between 0.1 to 15 milliliters per minute. The first flow rate may be 15 milliliters per minute and above. In some embodiments, the sample inclusion parameters can be measured at both sample flow rates with necessary corrections applied to account for the flow rate effect on sensitivity and measurement. Furthermore, the time synchronization of measurements with the sample flow rate values may be used. This can be achieved by controlling the measurements and flow rates by a computer, which is used for synchronization.

Achieving different flow rates within the particle monitoring system can be accomplished by different sample delivery options in addition or instead of partial diversion of the total sample flow. For example, in a single sample delivery option, different flow rates are achieved by the same delivery mechanism. Examples of such mechanisms include, but are not limited to, flow controllers, peristaltic or other type of pumps operating under control or in synchronization with measurement system, such as a computer system. The delivery mechanism is operable to change the flow rates, e.g., from the transport rate to the analysis rate and back to the transport rate.

In some embodiments, dual sample delivery option involving two different delivery mechanisms may be used, e.g., one for the first (transport) flow rate and another one for the second (analysis) flow rate. For example, flow rates for flow controllers may be above 10 milliliters per minute, so such tools can be used for sample transport at rates above 15 milliliters per minute. On the other hand, syringe pumps can be used at low flow rates of 5 ml/min and below and may be used for sample analysis as further described below with reference to FIGS. 4, 5 and 6. Dual sample delivery means also requires strong synchronization of operation of all pumps and sample analyzing means.

In some embodiments, the number of operational flow rates can be more than two.

DETAILED DESCRIPTION OF EXAMPLE EMBODIMENTS

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Introduction

As noted above, characterization of liquid samples having inclusions is important for many applications and industries. For purposes of this disclosure, the inclusions may be liquid inclusions (e.g., forming emulsions with a base liquid) and/or solid inclusions (e.g., forming slurries with a base liquid). In some embodiments, a liquid sample may include multiple different types of inclusions in the same sample, such as various combinations of liquid and solid inclusions in the same base liquid.

Some specific examples of inclusions and carrier liquids include, but are not limited to, slurries used in Chemical Mechanical Planarization (CMP). In this example, the liquid may include solid inclusions forming abrasive and corrosive chemical slurry (e.g., a colloid) in conjunction N a polishing pad and a retaining ring.

Another example is a lipid emulsion or a fat emulsion, which refers to an emulsion of lipid for human intravenous use. One specific example is a INTRALIPID® (supplied by Baxter International Inc. in Deerfield, Ill.), which is an emulsion of soy bean oil, egg phospholipids and glycerin, and is available in 10%, 20% and 30% concentrations.

Inclusion parameters, such as concentration and size distribution of inclusions, may vary for different applications. Many liquid samples of interest, for example slurries used in Chemical Mechanical Planarization (CMP), have concentrations of inclusions in range of 0.1% to 50%, with number concentration usually greater than $10^{12}$ particles per milliliter and inclusions in size range from 10 nanometers to 10 micrometers or, in some embodiments, greater than 10 micrometers. Such samples will be referred below as liquids with high concentration inclusions (HCI).

Figure 1A:
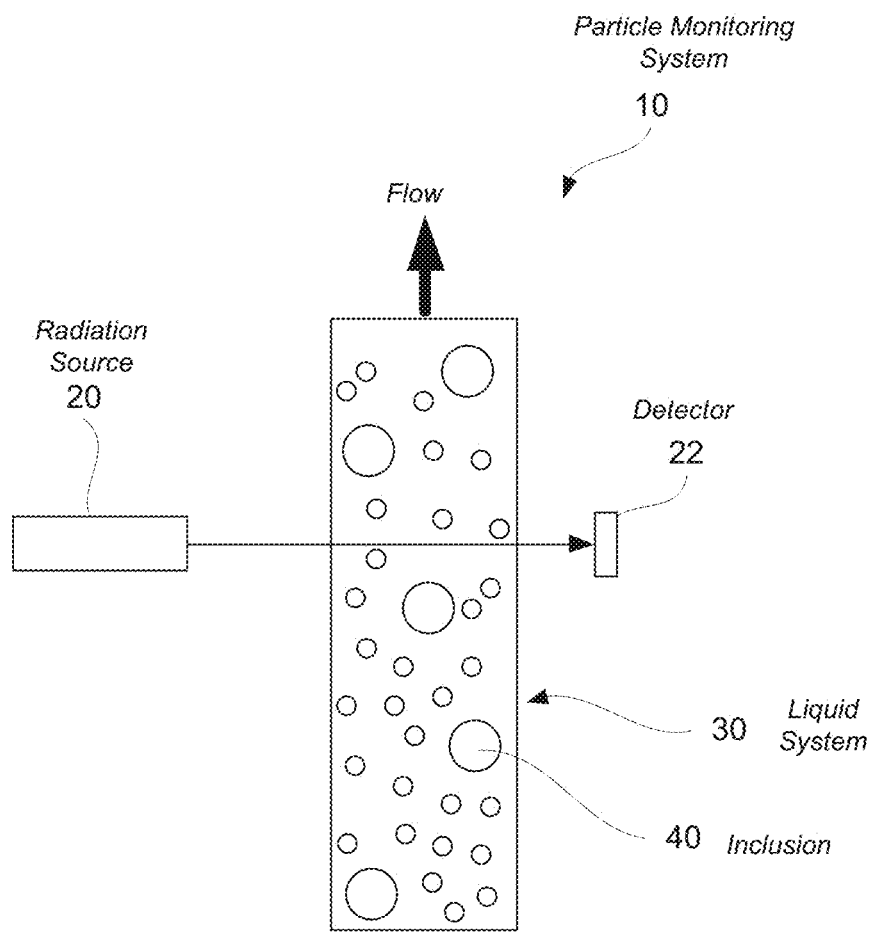
FIGS. 1A-1C are conceptual representations of a particle monitoring system illustrating effects of inclusions in liquid samples on measurement accuracy, in accordance with some embodiments.

FIG. 1A is a conceptual representation of particle monitoring system 10 for analyzing liquid system 30, in accordance with some embodiments. Particle monitoring system 10 may include radiation source 20 and detector 22. Some examples of radiation source 20 include, but are not limited to, lasers, light emitting diodes (LED), and lamps. Radiation source 20 may emit light at various wavelengths, such as visible range (400-800 nanometers), ultraviolet range (100-400 nanometers), infrared radiation (800 nanometers −1 micrometer), and various combinations thereof.

Detector 22 may be a single particle optical sensor. This sensor type may use single inclusion 40 passing through the radiation path for accurate measurements. The concentration limits for this sensor type is often $10^4$ particles per milliliter. At the same time, many liquid samples of interest have concentrations of inclusion greater than $10^{12}$ particles per milliliter far exceeding the limits of single particle optical sensors. Various conventional techniques for sample analysis, such as dilution, are not suitable for such vast differences between actual concentrations and detector limits.

In some embodiments, solid inclusions 40 in liquid system 30 are solid particles or, more specifically, nanoparticles. One specific example is silica nanoparticles, which form slurries when combined with a liquid medium. The silica nanoparticles may have a mean particle size of 30 nanometers to 100 nanometers. However, one having ordinary skill in the art would understand that other types of particles and/or nanoparticles as well as particle sizes are also within the scope of this disclosure. Furthermore, one having ordinary skill in the art would understand that actual particle sizes vary and often follow some particle size distribution.

Figure 1B:
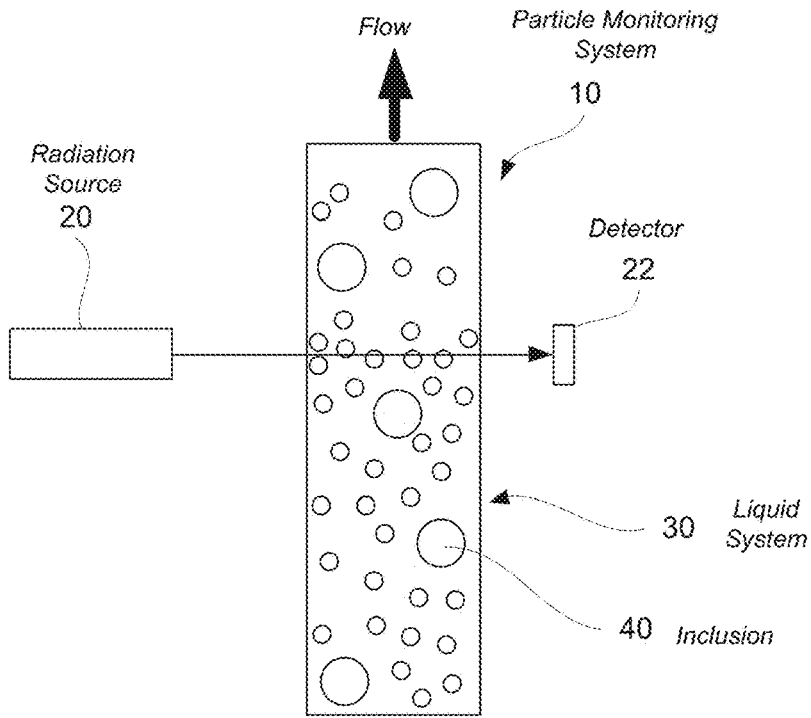

Referring to FIG. 1B, when small inclusions 40 are present in liquid system 30 at high concentrations, these inclusions 40 may scatter the same amount of light as large inclusions 40 resulting in mis-sized characterization. In other words, slurries having high concentrations of small particles may be characterized as slurries containing large particles.

Figure 1C:
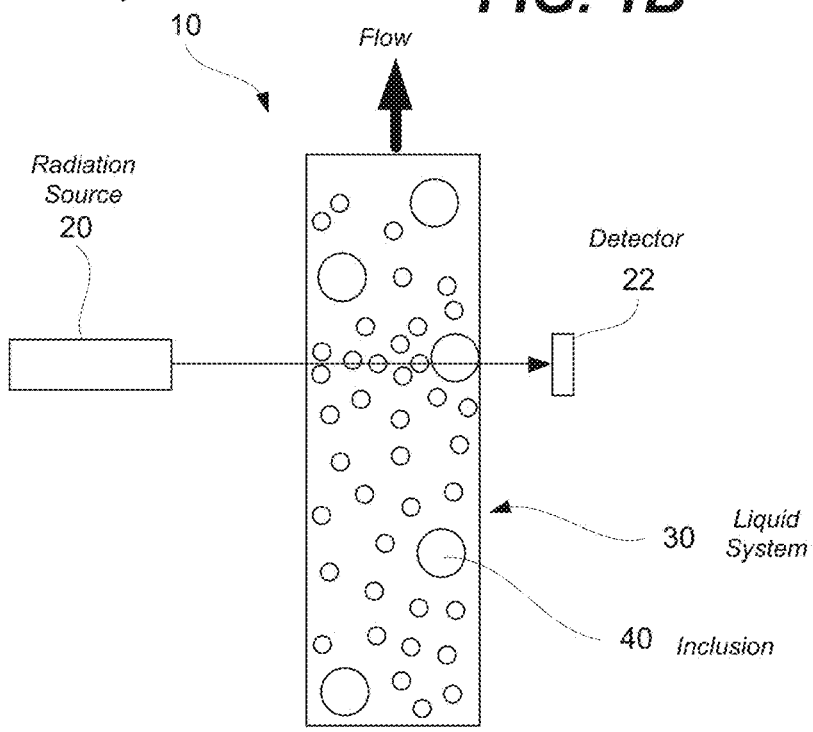

Referring to FIG. 1C, small inclusions 40 present at high concentrations may also mask large inclusions 40. This masking may result in undercounted characterization of at least large inclusions 40 in liquid system 30. Both effects shown and described with reference to FIGS. 1B and 1C may greatly reduce measurement accuracy.

Overall, the concentration, particle size distribution, and in some embodiments, the sample flow rate complicates the characterization of the particles and reduces accuracy. The combination of these factors, such as wide distribution of particle sizes and high flow rates may be particularly challenging for accurate measurements, yet very common in many applications. Various examples of the method and system described herein substantially improve measurement accuracy for such samples.

A brief review of a particular liquid sample may be helpful to better understand various aspects of this disclosure. In some embodiments, a liquid sample is an HCI liquid. Different inclusions in this sample may affect the sample performance in a wide dynamic range. For example, a CMP slurry may have a mean particle size of 50 nanometers and a particle concentration of up to $10^{15}$ particles per milliliter. The CMP performance of such slurry is greatly affected by the presence of larger particles even at smaller concentrations. As such, the size distribution, in particular, the mean particle size from 100 to 1000 nanometers with the concentration variation from $10^{10}$ to $10^2$ particles per milliliter, may need to be measured as a part of the overall CMP process. Furthermore, slurry aggregation during CMP may cause scratches and product defects. Defects characterization may be established by measuring the concentration and size distribution of particles in range from 1 to 10 micrometers. The particles concentration in that range may be in order of few particles per milliliter or below. Thus, the measured concentration range may be 10-12 orders of magnitude, which is challenging (if possible at all to measure with conventional techniques. For example, and as described above, high concentrations of inclusions may limit effectiveness of conventional optical methods for characterizing highly concentrated inclusions in liquid samples, even though optional methods have a non-destructive nature.

It has been shown experimentally that using a television system to analyze an optical signal scattered by particles allows to increase the signal/noise ratio by approximately 1000 times. This increase provides a unique opportunity to detect nanometer-sized particles. This measurement is based on dividing the total sensing volume into approximately $10^3$-$10^4$ smaller sub-volumes. The optical signal from each sub-volume is registered independently, resulting in the abovementioned signal/noise ratio increase. This approach can be used for detecting the signals from small particles of high concentration and big particles of low concentration and preventing them from interfering with each other.

Figure 2:
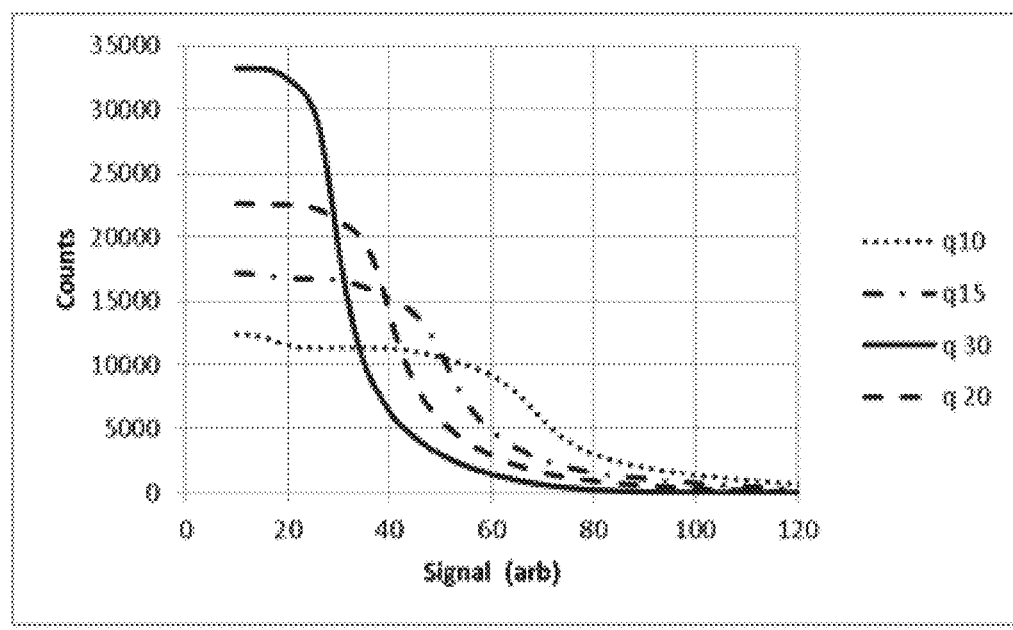
FIG. 2 illustrates plots of measured concentrations of the same particles for different flow rates. Higher flow rate results in more counts of particles while signal from particles shifts to lower values

Another factor in characterizing liquid samples is the flow rate of the measured sample. In some applications, a static (not flowing) sample is not available and the measurement has to happen while the sample is flowing. Without being restricted to any particular theory, it is believed that several characteristics of a device and/or a method for analyzing of HCI liquid samples depend on the sample flow rate. Analyzing at lower flow rates generally yields a stronger signal enabling more precise measurements of smaller inclusions having higher concentrations, as can be seen, from the experimental data presented in FIG. 2. At the same time, higher flow rates may be used to measure inclusions having lower concentrations. Thus, the flow rate for sample analysis may depend and may be changes based on sample characterization goals and characteristics of a particular sample. In some applications, the sample flow rate may be defined by various factors, such as keeping the sample integrity. For example, particles in CMP slurries have tendency to settle down by gravitational force. Oxide slurries based on silica abrasive are best suspended due to zeta potential on the particle and lower density (~2.2 g/cm$^3$) compared to alumina (~4.0 g/cm$^3$) or ceria (~7.6 g/cm$^3$). Since practically all slurries have some degree of distribution of particle sizes, large particles may settle faster without sufficient means to keep them dispersed. Typically, slurries are flown faster than 1 ft/sec to maintain uniform dispersion of all particles throughout the entire volume of the slurry. For example, Required Minimum Flow Velocity (RMFV) from 0.5 ft/sec for most of silica slurries to 2.5 ft/sec for ceria slurries may be used. As such, if measurement is performed at a flow rate below 18-45 ml/min (for a sample tubing of 1/16" ID), the measured particle content may differ from the bulk sample that is flown at faster rates.

A factor used for estimating Required Minimum Flow Velocity (RMFV) may be based on the fact that there is some physical distance between the measurement device and the sample source. This distance results in the time difference between the sample extraction and analysis. For example, in most cases, the distance between a measuring device and a sample source is in the range of 3-5 ft. With that distance and the flow velocity of 0.5 ft/sec, the time gap may be 6-10 sec. This time gap may be a substantial limiting factor for real time sample monitoring systems. At the same time, lower flow rates (e.g., less than 1-5 ml/min) may be used to advance the upper limit of particles concentration.

While inclusions described herein are often referred to as nanoparticles, one having ordinary skills in the art would understand that other types of particles (e.g., particles having a mean particle size of greater than 1 micrometer) or liquid inclusions are also within the scope. Furthermore, all nanoparticle characterization methods and systems described herein can apply to emulsions as well.

Apparatus Examples

Figure 3:
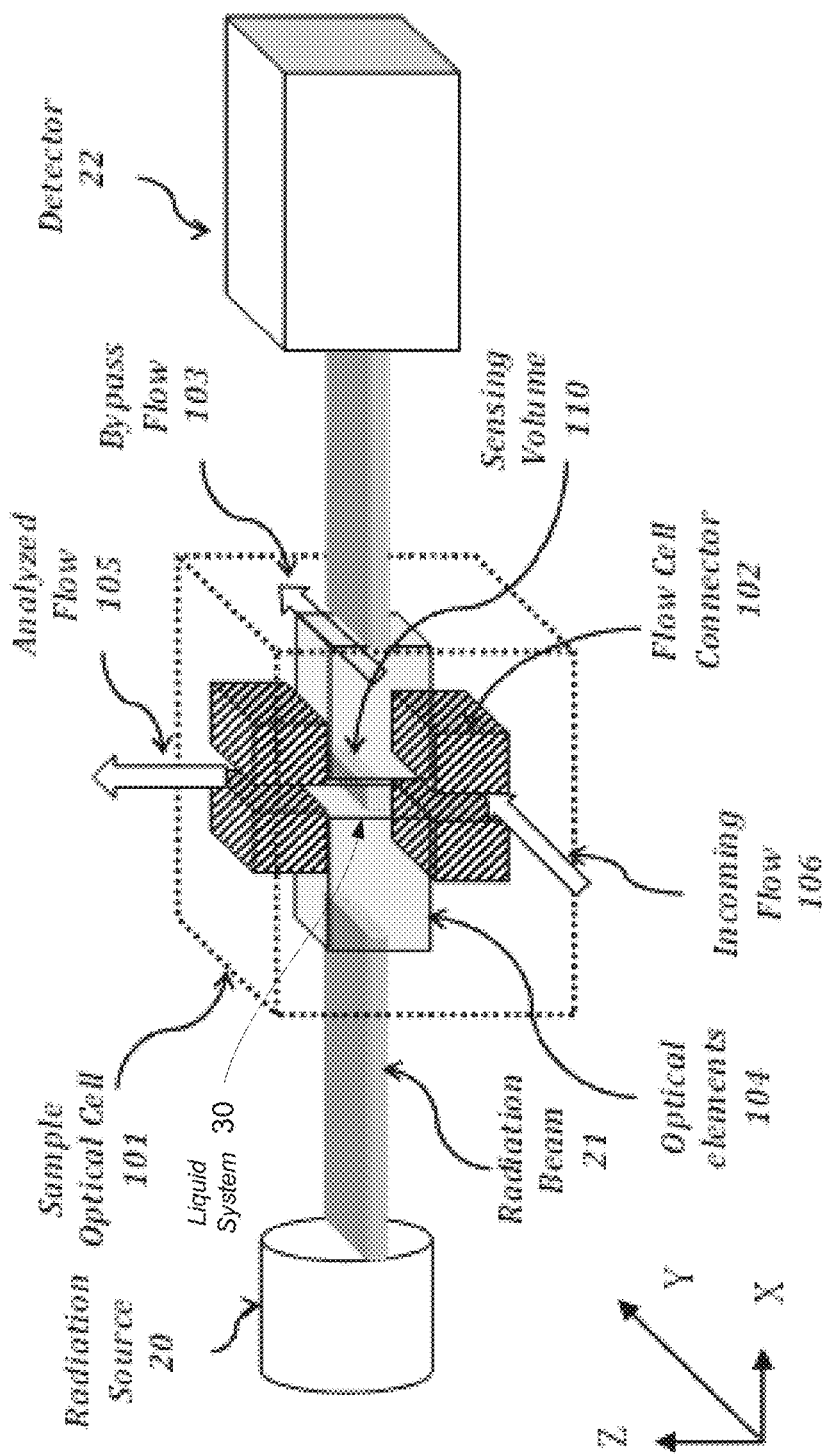
FIG. 3 is a conceptual representation of a particle monitoring system illustrating flow splitting aspects, in accordance with some embodiments.

FIG. 3 is a simplified schematic representation of particle monitoring system 100, in accordance with some embodiments. Some aspects of particle monitoring system 100 are described above with reference to FIGS. 1A-1B. Specifically, particle monitoring system 100 may comprise radiation source operable to emit radiation beam 21. Particle monitoring system 100 also comprises detector 22 operable to receive signal from liquid system 30 after being illuminated by radiation beam 21.

Particle monitoring system 100 may receive incoming flow 106 of the liquid sample into first flow cell connector 102. First flow cell connector 102 may divide incoming flow 106 into at least two portions, i.e., a portion directed through a channel formed by optical elements 104 and into a portion forming bypass flow 103. The portion passing through optical cell 101 (defined by sensing volume 110) is analyzed using one or more optical techniques, such as light scattering or extinction, e.g., through a window provided in optical cell 101. For example, optical cell 101 may be coupled to radiation source 20 with radiation beam 21 and detector 22 also as shown in FIGS. 1A-1C. One having ordinary skills in the art would understand that optical cell 101 show in FIG. 3 is a components of particle monitoring system 100 shown in FIGS. 1A-1C. However, the specific aspects of flow control achieved with particle monitoring system 100 allow overcoming various issues associated with conventional monitoring systems that are described above.

Detector 22 may be configured to perform time resolved measurements. That portion goes through second flow cell connector 102 to a sample handling device (not shown). Bypass flow 103 goes particle monitoring system 100 without entering optical cell 101.

Figure 4:
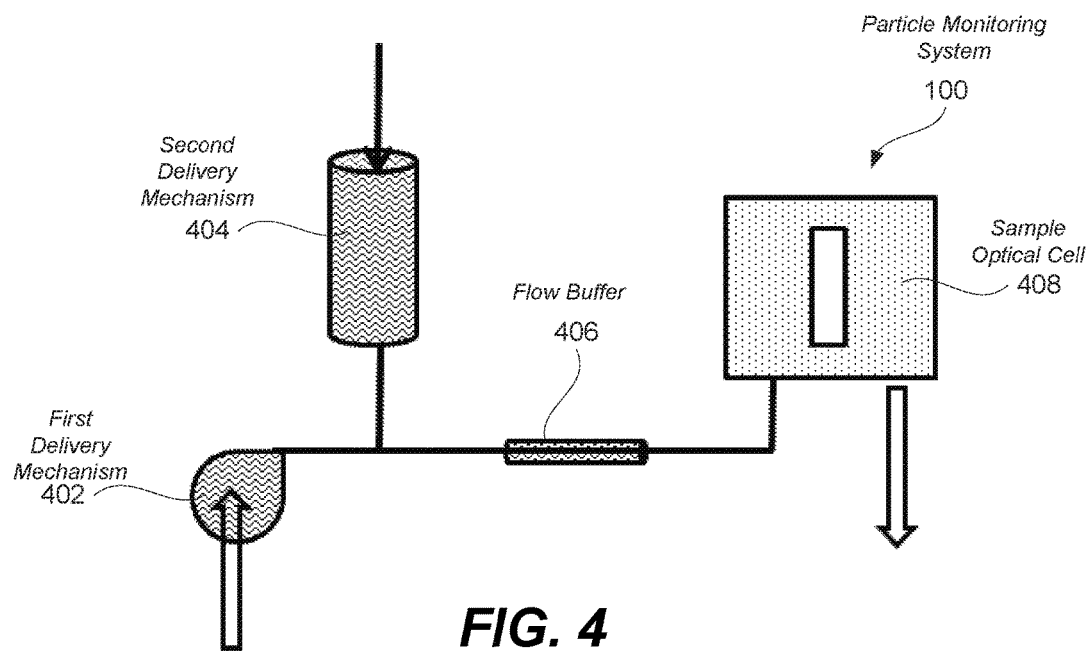
FIGS. 4-6 are conceptual representations of a particle monitoring system illustrating different aspects of multiple flow delivery mechanisms, in accordance with some embodiments.

FIG. 4 is a simplified schematic representation of particle monitoring system 100, in accordance with some embodiments. A liquid sample may be delivered into particle monitoring system 100 using first delivery mechanism 402, which may be a peristaltic pump or any other suitable pump. This liquid sample may be delivered at a first flow rate, and the delivery may stop at some point. As noted above, the first flow rate may be selected to ensure integrity of the liquid sample during its transport and the first delivery mechanism 402 may be selected to ensure this flow rate.

While first delivery mechanism 402 is stopped, second delivery mechanism 404 may deliver liquid through particle monitoring system 100 at a second flow rate. The second flow rate may be specifically selected to achieve accurate characterization of the sample and may be different form the first flow rate. Second delivery mechanism 404 may be a syringe pump or any other suitable pump capable of delivering the sample through particle monitoring system 100 at the second flow rate. In this example, the portion of the liquid sample accumulated in connecting tubes may be in very close vicinity of particle monitoring system 100, and it will not alternate parameters while being transported through particle monitoring system 100 and analyzed.

In some embodiments, deionized water or other liquid compatible with the liquid sample can be used to push the sample through particle monitoring system 100. That pushing liquid will also pass through particle monitoring system 100 and eventually will be measured in this embodiment. Accordingly, corrections should be made in the sample characterization data to separate the data corresponding to the liquid sample from the data corresponding to the pushing liquid.

Figure 5:
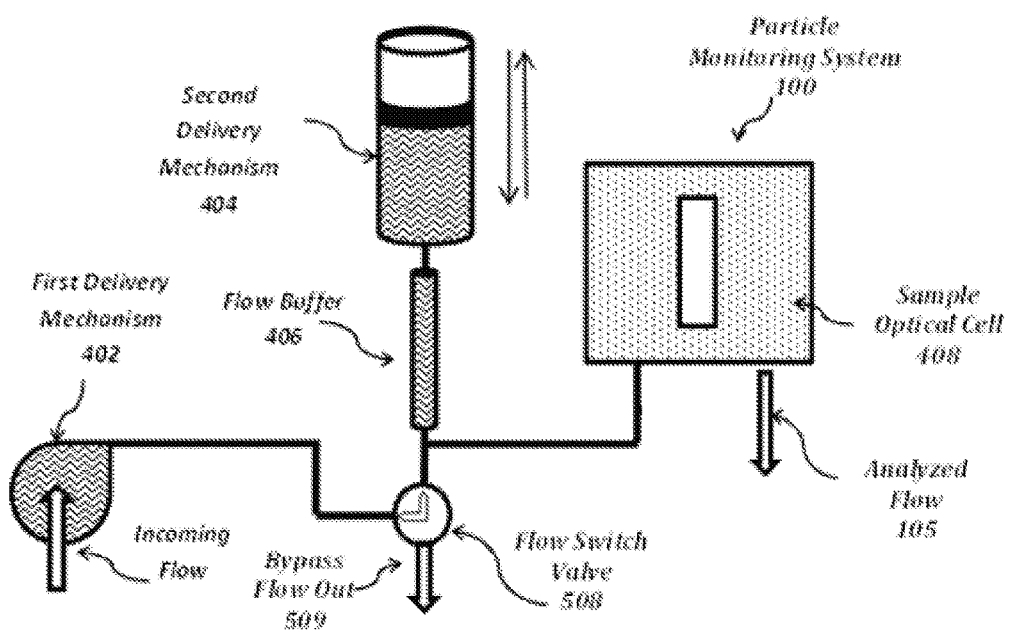

FIG. 5 is a simplified schematic representation of particle monitoring system 100, in accordance with some embodiments. In this example, the sample itself can be used as pushing liquid referring to the system described above with reference to FIG. 4. This can be accomplished by withdrawing a part of sample by second delivering mechanism 404 into flow buffer 406 while the majority of sample is delivered through sample optical cell 408 at high (transport) flow rate. At second phase of measurement the first delivery mechanism is stopped and sample is delivered from buffer 406 into sample optical cell 408 at low (measurement) flow rate. The second phase should be relatively short in time (preferably 0.1 to 5 seconds) to preserve the sample integrity and to avoid slurry settling.

In some embodiments, flow switch valve 508 can be used to divert the main slurry flow to bypass out 509 during sample measurement phase keeping the first delivery mechanism 402 operating at set flow rate. The advantage of this embodiment is continuous sample flow through the communication lines without any interruptions which may be essential for some samples (e.g., for heavy settling slurries).

Also, another liquid buffer can be used to manipulate the sample motion through particle monitoring system 100, for example, when the liquid sample is not compatible with flow handling means. For example, some slurries may be not used with syringe pumps. This can be accomplished by preliminary filling the second delivery mechanism 404 and flow buffer 406 with compatible buffer liquid (for example with deionized water) and setting the operational range of second delivery mechanism 404 such that sample will fill flow through buffer 406 but not reach second delivery mechanism 404 during withdraw (transport) phase. In delivery (measurement) phase the sample will be pushed out from flow buffer 406 providing necessary sample flow through sample optical cell 408. With correct operational range only sample will pass through optical cell while buffer liquid will stop at flow buffer 406.

Figure 6:
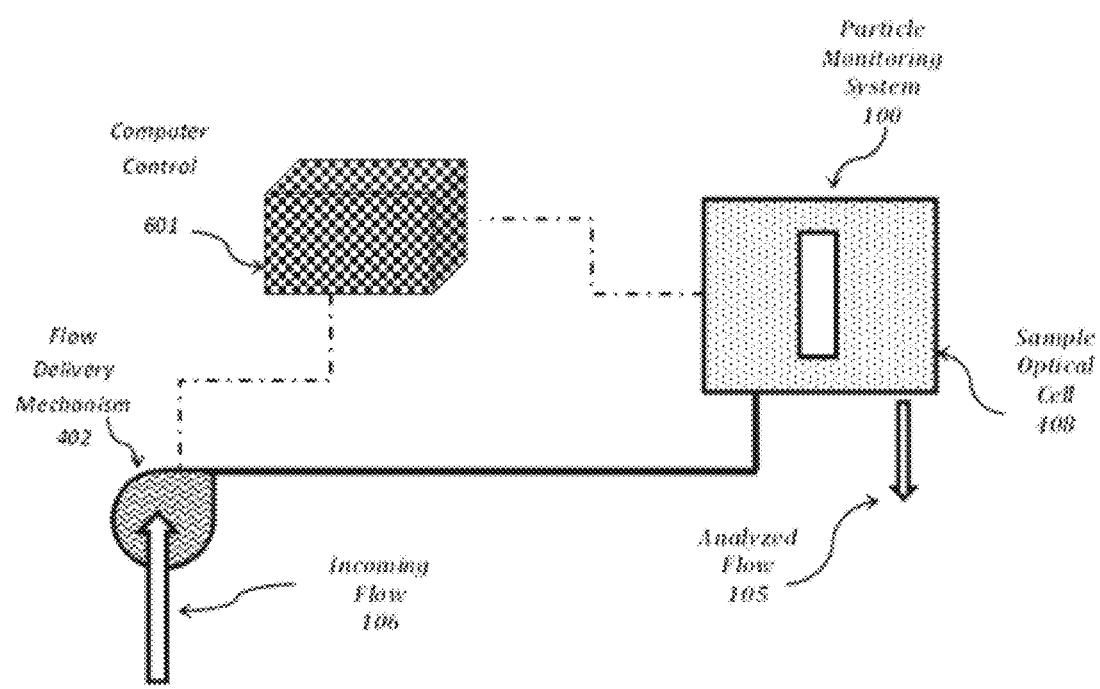

FIG. 6 is a simplified schematic representation of particle monitoring system 100, in accordance with some embodiments. A liquid sample may be delivered into particle monitoring system 100 using first delivery mechanism 402, which may be a peristaltic pump or any other suitable pump with variable flow rate controlled by computer 601 or another control devise synchronized with particle monitoring system 100. This liquid sample may be delivered at a first flow rate, and the delivery may switch to second flow rate at some point. As noted above, the first flow rate may be selected to ensure integrity of the liquid sample during its transport and the second flow rate can be selected to provide the optimal sample analysis.

Figure 7A:
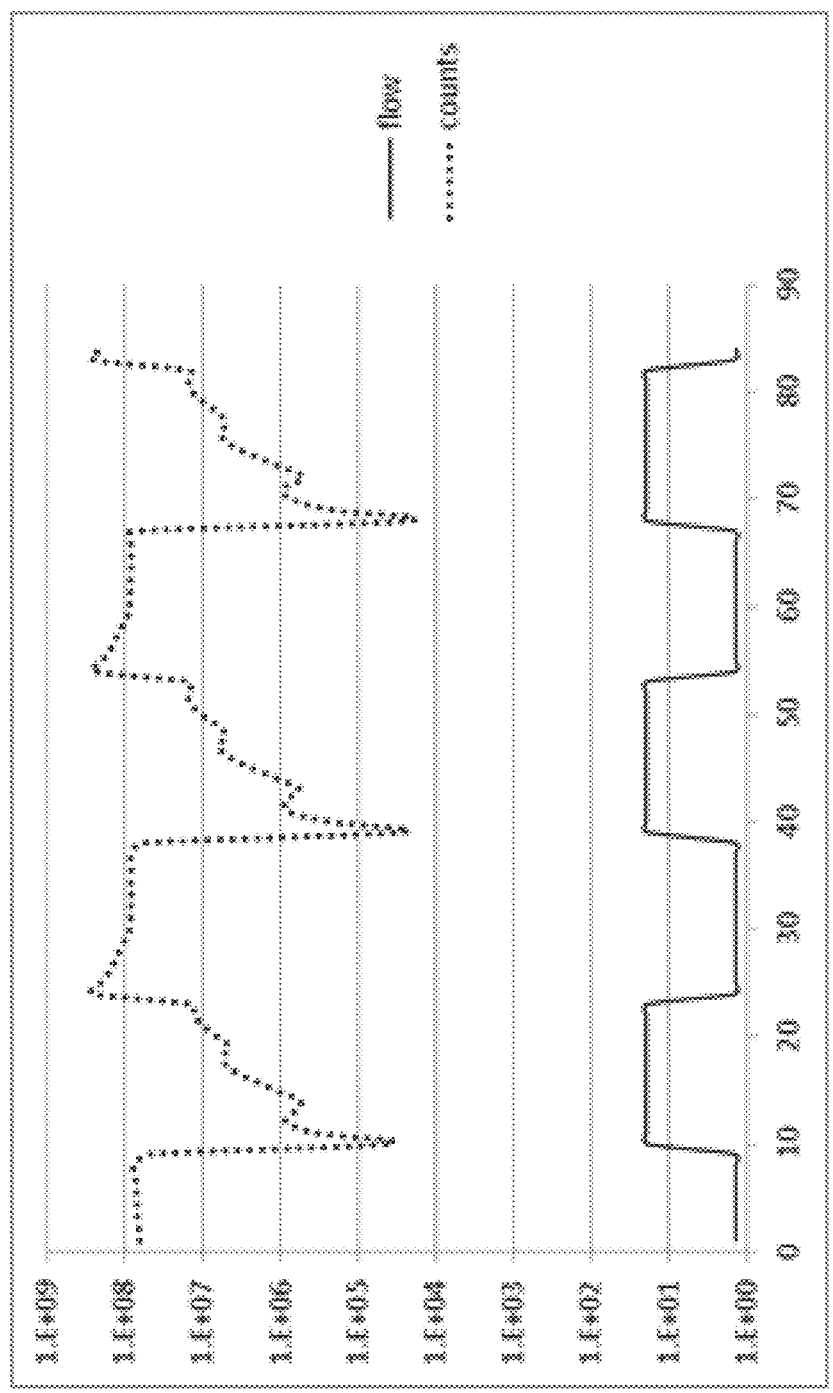
FIG. 7 illustrates plots of measured concentrations of particles at different flow rates of 15 ml/min (transport) and 1.5 ml/min (measurement). Data presented for slurry sample (A) and latex test particles (B). Latex test particles are stable and show no transition characteristics while in slurry sample the transition of parameters at beginning and at end of high (transport) flow regime is very well pronounced.
Figure 7B:
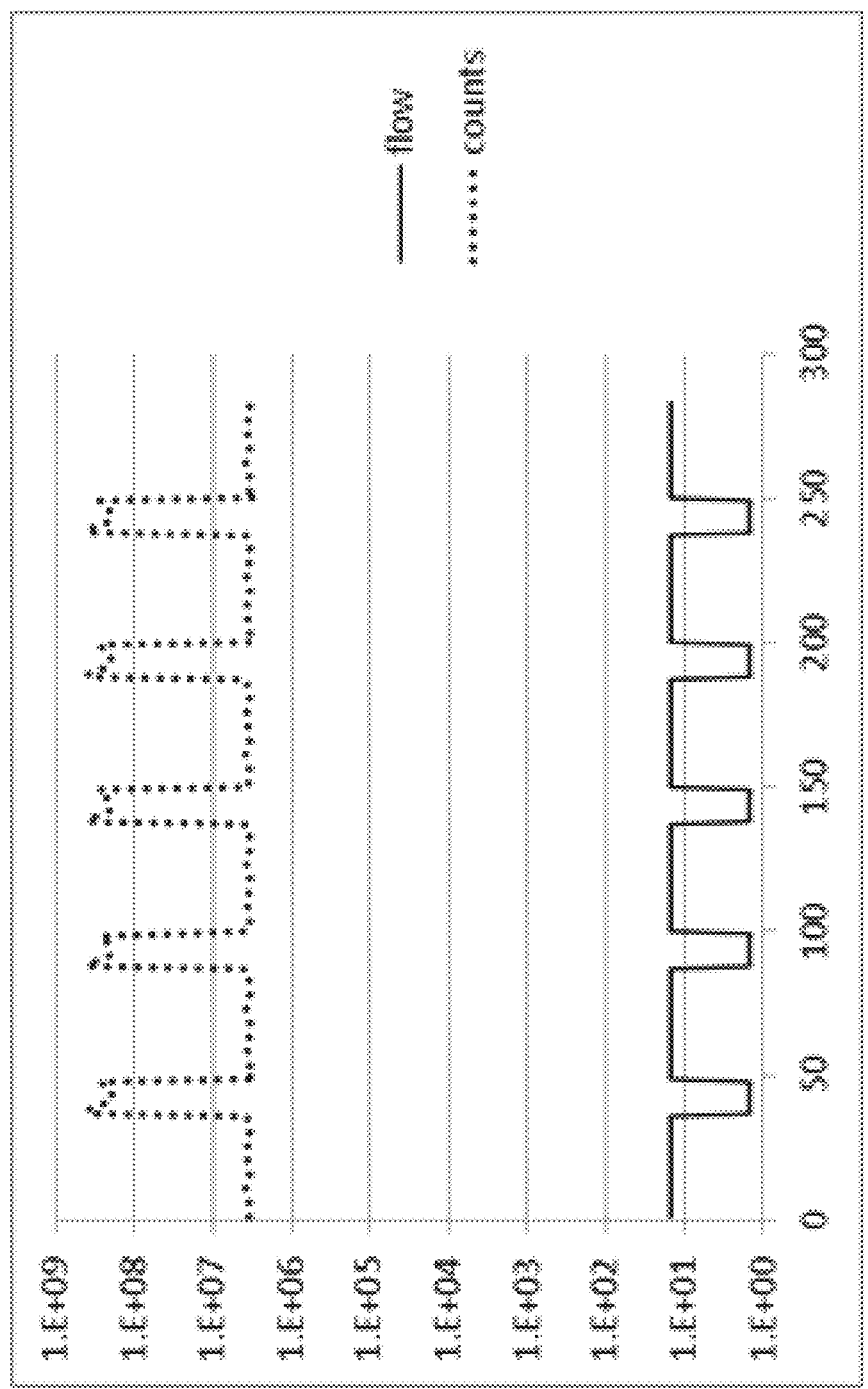

FIGS. 7A and 7B illustrate the data from particle monitoring system embodiment described in FIG. 6. The registered number of particles in a slurry sample (FIG. 7A) and polistyrol latex particles (PSL) (FIG. 7B) are presented along with sample flow rates. PSL test particles demonstrate very stable readings at high and low flow rates due to low settle velocity. Counts at high flow rate are lower than at low flow rate because of drop of particle monitoring system sensitivity at higher flow rates. Similar difference of counts at high and low flow rates for slurry sample (FIG. 7A) but also one can see the transition of counts during high flow rate phase which can be explained by deviation of sample parameters during slow flow rate phase.

Figure 8:
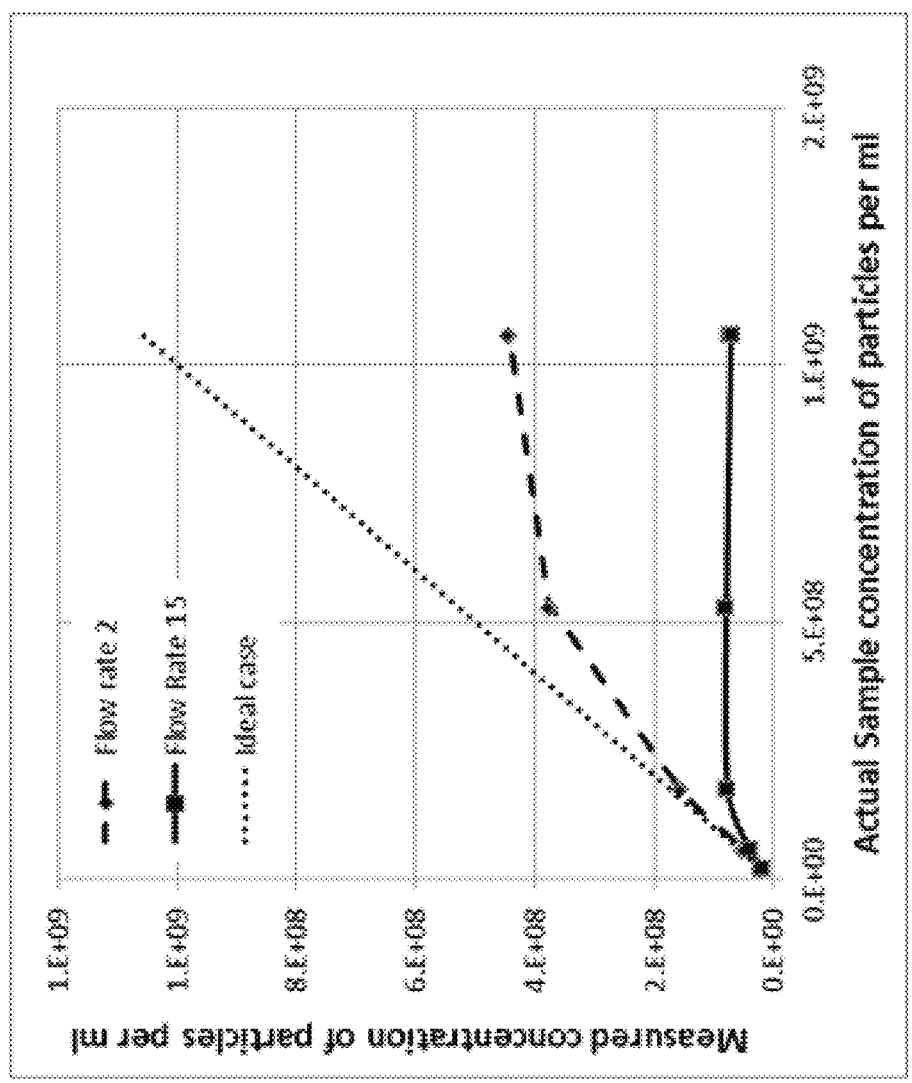
FIG. 8 illustrates plots of measured concentrations of particles relative to actual concentrations for different flow rates and effect of signal coincidence at high concentration of inclusions.
Figure 9:
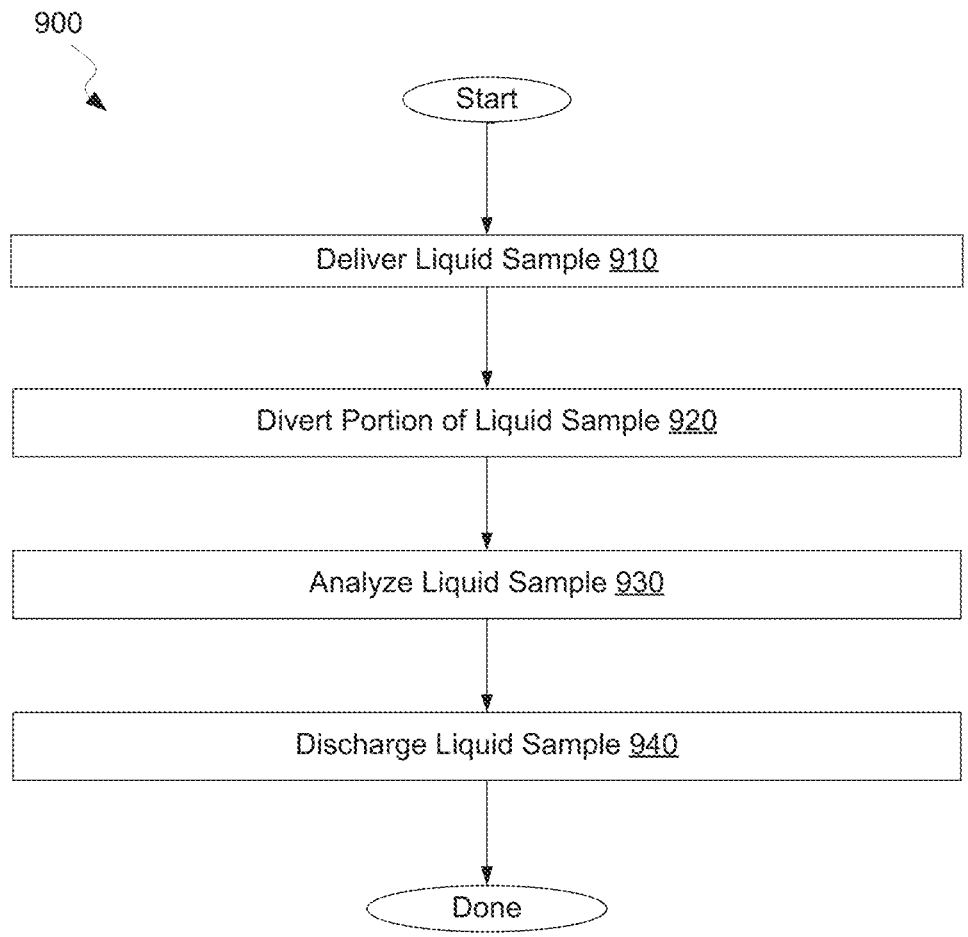
FIG. 9 is a process flowchart corresponding to method 900 for analyzing a liquid sample in a particle monitoring system, in accordance with some embodiments.

FIG. 8. illustrates another advantage at low flow rate operation. Presented is comparison of measured concentration of particles to actual sample concentration of particles in sample. One of limiting factors for analyzing of HCl liquid samples with SPOS is signal coincidence from particles which strongly depend on the sample flow rate. The signal coincidence results in deviation of measured number concentration of particles from actual ones as illustrated in FIG. 8. Data presented in FIG. 8 also illustrates that data loss due to coincidence strongly depends on flow rate confirming the conclusion of preferable analysis of HCl liquid samples at low flow rate Method Examples FIG. 9 is a process flowchart corresponding to method 900 for analyzing a liquid sample in a particle monitoring system, in accordance with some embodiments. Method 900 may comprise delivering the liquid sample to an inlet of the particle monitoring system (block 910). Various examples of the particle monitoring system and samples are described above.

Method 900 may further comprise diverting a portion of the liquid sample into an optical cell of the particle monitoring system (block 920). The liquid sample may be delivered at a first flow rate. However, the diverted portion of the liquid sample may be flown at a second flow rate different from the first flow rate. For example, the second flow rate may be less than the first flow rate. The second flow rate may be variable overtime for analyzing different size of particles in the liquid sample. In some embodiments, delivering the liquid sample to the inlet is performed using a first delivery mechanism. Flowing the liquid sample into the optical cell may be performed using a second delivery mechanism different from the first delivery mechanism.

Method 900 may comprise analyzing the sample in the optical cell (block 930). In some embodiments, the diverted portion of the liquid sample is analyzed in the optical cell while flown at the second flow rate. The second flow rate may be selected based on characteristics of the diverted liquid sample and a technique used for characterization of the diverted liquid sample. Analyzing is performed using time resolved measurements.

Method 900 may comprise discharging the liquid sample from the particle monitoring system (block 940). During this operation, the diverted potion of the liquid sample may be combined with the rest of the liquid sample.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. A particle monitoring system comprising:
   an inlet, for receiving a liquid sample;
   a first delivery mechanism, coupled to the inlet,
      wherein the first delivery mechanism is configured deliver a liquid sample to the inlet at a first flow rate, selected to maintain integrity of the liquid sample;
   a sample optical cell, coupled to the inlet for characterization of the liquid sample;
   a second delivery mechanism, coupled to the inlet,
      wherein the second delivery mechanism is configured deliver a portion of the liquid sample from the inlet to the sample optical cell at a second flow rate, selected to maintain the characterization accuracy of the sample optical cell and being different from the first flow rate; and
   a system controller, coupled to the sample optical cell and the deliver mechanisms, wherein the system controller is configured to variably control the first flow rate and the second flow rate.

2. The particle monitoring system of claim 1, wherein the first delivery mechanism is a peristaltic pump, controlled by system controller.

3. The particle monitoring system of claim 1, wherein the second delivery mechanism is a syringe pump, controlled by system controller.

4. The particle monitoring system of claim 1, wherein the second delivery mechanism is a second peristaltic pump, controlled by system controller and configured to operate at different flow rate than first peristaltic pump.

5. The particle monitoring system of claim 1, wherein the sample optical cell comprises a radiation source and a detector and configure to characterize the portion of the liquid sample passing through the optical cell.

6. The particle monitoring system of claim 5, wherein the detector is controlled by system controller and configured to perform time resolved measurements on the portion of the liquid sample passing through the sample optical cell such that the time resolved measurements is synchronized with the second sample flow rate.

7. The particle monitoring system of claim 5, wherein the detector is a light scattering detector or an extinction detector, controlled by system controller.

8. The particle monitoring system of claim 1, wherein the system controller is configured to variably control the second flow rate based on input from the sample optical cell.

9. The particle monitoring system of claim 1, wherein the system controller is configured to variably control the second flow rate based on one or more of particle concentration in the portion of the liquid sample and particle size distribution in the portion of the liquid sample.

10. The particle monitoring system of claim 1, wherein the system controller is configured to variably control the second flow rate based on a characterization technique of the sample optical cell.

11. The particle monitoring system of claim 1, wherein the inlet comprises a flow buffer, fluidly coupled the second delivery mechanism and configured to store a buffer liquid.

12. The particle monitoring system of claim 11, wherein composition of the buffer liquid is different from composition of the liquid sample.

13. The particle monitoring system of claim 11, wherein composition of the buffer liquid is same as composition of the liquid sample.

14. The particle monitoring system of claim 11, wherein the second delivery mechanism is configured to flow the buffer liquid out of the flow buffer at the second flow rate.

15. The particle monitoring system of claim 11, wherein the flow buffer couples the second delivery mechanism to the inlet.

16. The particle monitoring system of claim 11, wherein the flow buffer is a part of the inlet.

17. The particle monitoring system of claim 1, wherein the inlet comprises a bypass, configured to divert a remaining portion of the liquids sample away from the sample optical cell.

18. The particle monitoring system of claim 17, wherein the bypass is coupled to a flow switch valve, configured to control the first flow rate while delivering the portion of the liquid sample from the inlet to the sample optical cell at the second flow rate.

19. The particle monitoring system of claim 1, wherein the first flow rate is selected to ensure integrity of the liquid sample while the liquid sample flows through the inlet.

20. The particle monitoring system of claim 1, wherein the second delivery mechanism is configured deliver the portion of the liquid sample from the inlet to the sample optical cell for a period of time between 0.1 seconds and 5 seconds.

* * * * *